United States Patent [19]

Kessel

[11] Patent Number: 4,662,216
[45] Date of Patent: May 5, 1987

[54] ROCKET EXHAUST PROBE

[75] Inventor: Philip A. Kessel, Lancaster, Calif.

[73] Assignee: The United States of America as represented by the Secretary of the Air Force, Washington, D.C.

[21] Appl. No.: 817,714

[22] Filed: Jan. 10, 1986

[51] Int. Cl.$^4$ ............................................. G01M 15/00
[52] U.S. Cl. .................................. 73/116; 73/863.12; 73/863.23; 73/863.55
[58] Field of Search ............... 73/116, 863.11, 863.12, 73/863.21, 863.22, 863.23, 863.24, 863.25, 866.5, 863.41, 863.51, 863.52, 863.55; 55/274

[56] References Cited

U.S. PATENT DOCUMENTS

| | | |
|---|---|---|
| 984,047 | 2/1911 | Touzalin . |
| 3,011,336 | 12/1961 | Weiss ........................................ 73/29 |
| 3,152,479 | 10/1964 | Small ................................... 73/863.12 |
| 3,802,167 | 4/1974 | Turman ................................ 55/396 |
| 3,938,390 | 2/1976 | Grey ................................. 73/763.11 |

Primary Examiner—Jerry W. Myracle
Attorney, Agent, or Firm—Jules J. Morris; Donald J. Singer

[57] ABSTRACT

A rocket exhaust probe 10 for collecting particulates from a rocket exhaust plume. The probe comprises a tungsten nose tip 18, a tip holder 20, a probe body 22 and a tail section 24. Rocket exhaust gas enters the probe at the nost tip inlet 32 and passes into a mixing chamber 36 where the exhaust gas mixes with an inert cooling gas that cools and decelerates the exhaust gas. The mixture of exhaust gas and inert gas then passes into a diffusion chamber 50 where it further cools and decelerates before passing through a submicron particle collection filter 52.

17 Claims, 2 Drawing Figures

ROCKET EXHAUST PROBE

STATEMENT OF GOVERNMENT INTEREST

The invention described herein may be manufactured and used by or for the Government for governmental purposes without the payment of any royalty thereon.

TECHNICAL FIELD

This invention relates to test instrumentation and particularly to instrumentation used to investigate test rocket operation and performance.

BACKGROUND OF THE INVENTION

Rocket testing is a particularly difficult and costly operation. Rocket operation, however, must be thoroughly understood during the test and development phase in order to insure successful launching. Unpredicted or improper rocket operation can result in a variety of problems including failure to reach correct orbit or location, lack of control, overheating and premature shutdown.

Collecting data during rocket tests is a particularly difficult task because of the extremely hostile environment created by rocket ignition; this is particularly true in close proximity to the rocket nozzle where rocket exhaust plume temperatures are in the range of 3,000° C. (6,000° R.) Sensing the environment of the rocket exhaust plume would provide important information that would be helpful in analyzing rocket combustion and performance. Such information would undoubtedly include examining rocket exhaust particles and determining the mass flux distribution in the exhaust plume. Prior to use of the invention disclosed herein conventional pitot tubes and filters have been placed to collect similar data at locations distant from rocket exhaust nozzles where exhaust temperatures are reduced to near ambient temperatures.

The use of conventional probes has had distinct disadvantages due to their inability to withstand the rocket plume environment adjacent to rocket exhaust nozzles. An important disadvantage is their inability to capture an unbiased exhaust stream that hasn't been substantially attenuated and mixed with outside air. It is believed that exhaust particles carried by the exhaust stream react with air and depart the exhaust stream prior to reaching the conventional probes.

Another problem occurs when collecting particles from the exhaust stream. Particles in the rocket plume can travel in excess of six times the speed of sound. At such speeds the particles easily melt or penetrate any filter placed in their path, making collection exceedingly difficult.

A further problem with probes for use in fast moving exhaust streams is that most such probes are incapable of ingesting high speed air without aerodynamically choking. Choking the inlet flow results in much of the airstream being diverted around the probe and thereby biasing the data collected.

In view of the above it is an object of the present invention to provide a data collection probe capable of withstanding the hostile environment of rocket exhaust plume for a tixe sufficient to collect an unbiased exhaust plume sample.

Another object of this invention is to provide a data collection probe which successfully collects exhaust particles on a submicron mesh filter.

A further object of this invention is to provide a probe which is capable of ingesting high speed air flows without choking.

SUMMARY OF THE INVENTION

The invention comprises a probe to sample gas and particles from a supersonic stream of gas exhausted by a rocket nozzle. The probe utilizes a nose tip of tungsten capable of withstanding the rocket plume environment for at least 1.0 seconds while ingesting at a central inlet a rocket plume exhaust stream. The body of the probe is cooled by an inert coolant gas which flows exteriorly to cool a portion of the probe nose.

An aspect of the preferred embodiment is that the nose tip has a sharp leading edge to avoid the formation of a local bow shock that would bias ingestion of particles. The nose tip's inlet passage is also designed to prevent boundary layer growth from choking the inlet airflow.

In the preferred embodixent of the invention the inert coolant gas all flows through an internal mixing chamber where it mixes with the ingested inlet gas sample to cool and decelerate the inlet gas. The mixed inlet and inert gas stream then enters a diffusion chamber at near sonic speed and further decelerates before flowing through a filter that collects particles.

Preferably the filter is of a small mesh and retains particles smaller than one micron without causing undue resistance to the passage of gas.

The preferred embodiment of the invention also comprises static pressure measurement sensors adjacent to the mixing chamber so that the inert gas flow can be monitored and controlled to optimize the mixing of inert gas with the exhaust gas. It is also intended that a lower than ambient pressure be maintained at the probe inlet to facilitate exhaust gas ingestion without choking.

BRIEF DESCRIPTION OF THE DRAWINGS

The foregoing and other objects and advantages of the invention will be apparent from the following more particular description of the preferred embodiment of the invention, as illustrated in the accompanying drawings, in which like reference characters refer to the same parts throughout the different views. The drawings are not necessarily to scale, emphasis instead being placed upon illustrating the principles of the invention.

DETAILED DESCRIPTION OF THE INVENTION

Figure 1:
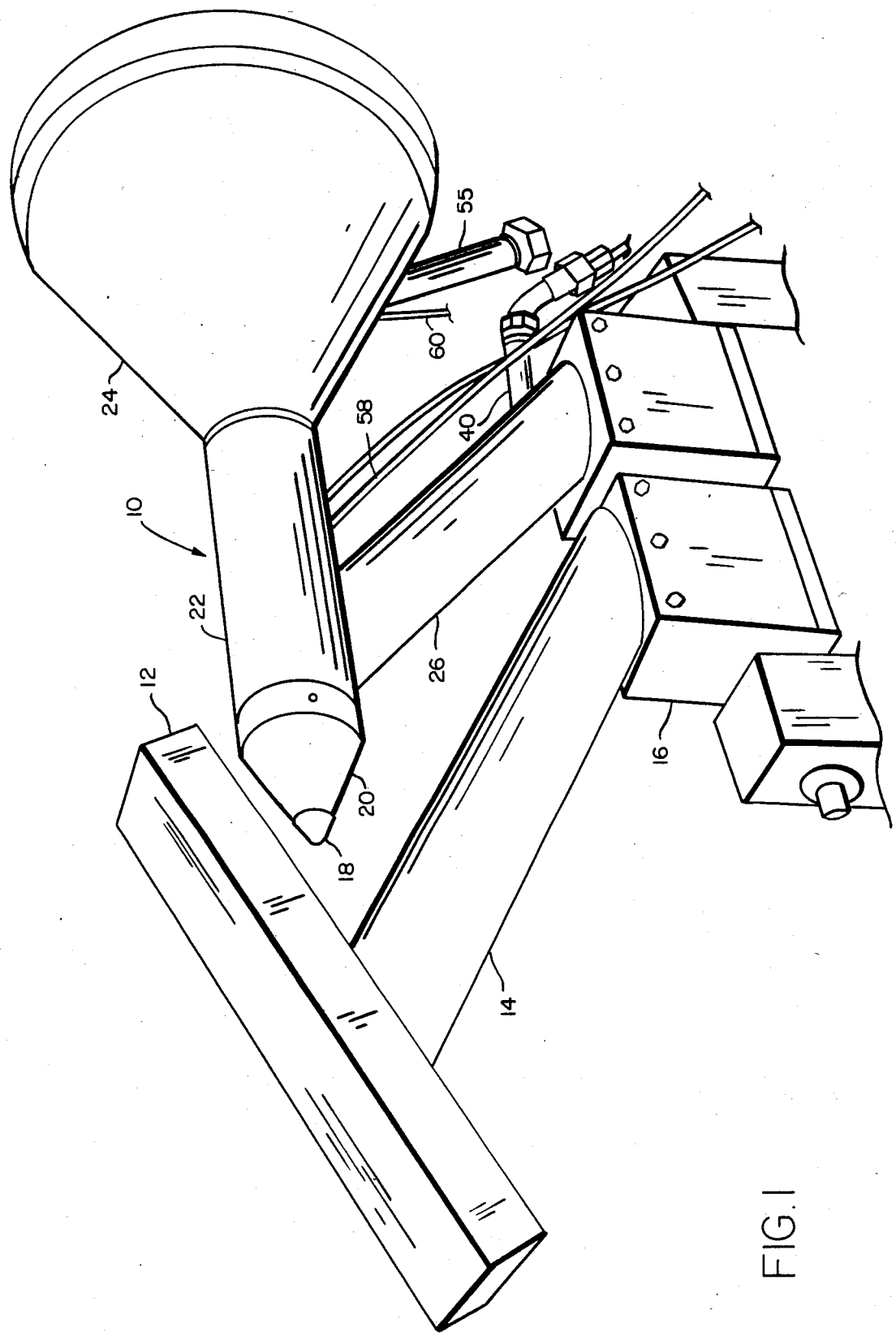
FIG. 1 is a perspective view of a rocket exhaust probe and its protective shield.
Figure 2:
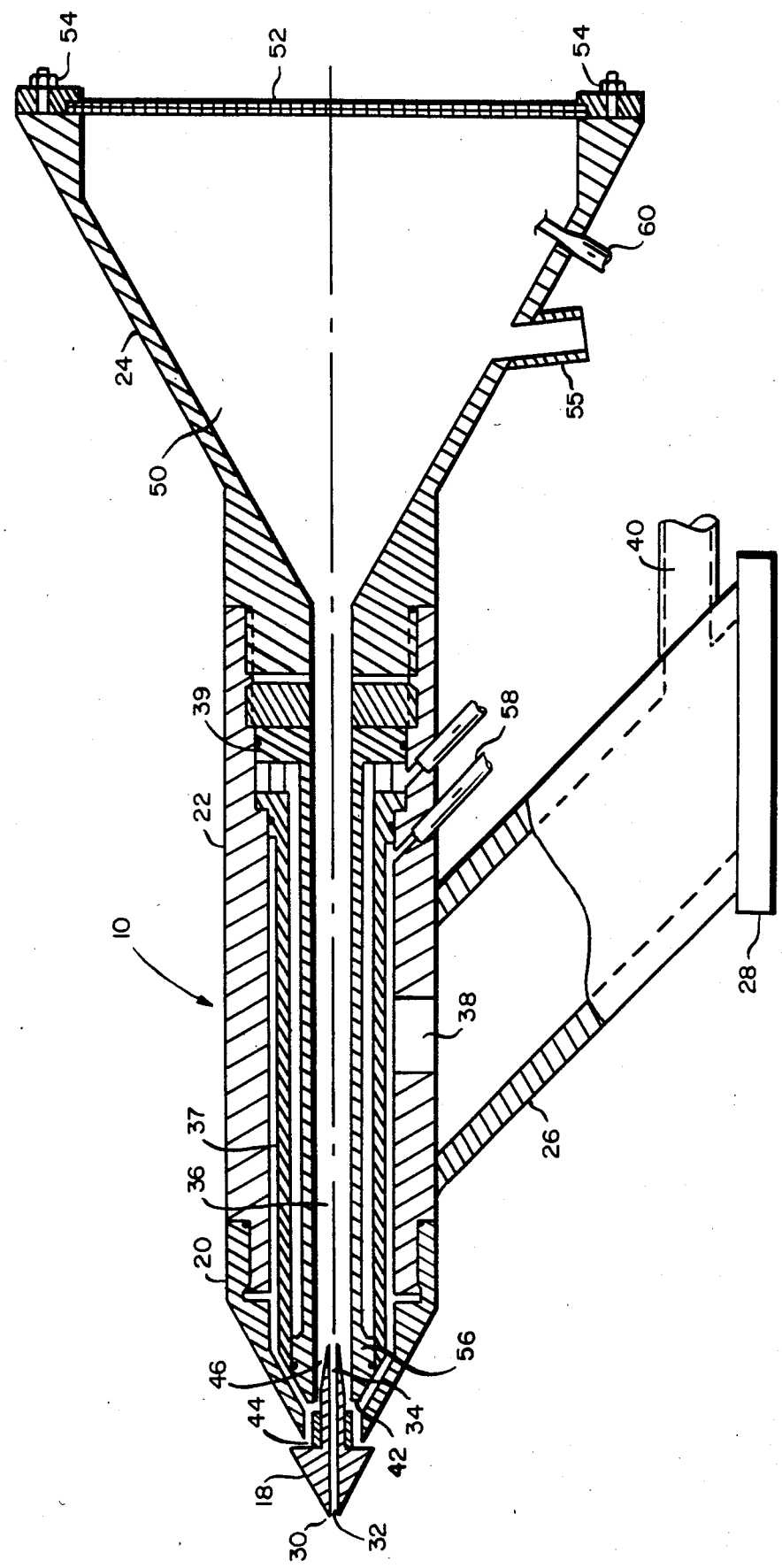
FIG. 2 is a cross section of the rocket exhaust probe of FIG. 1.

FIGS. 1 and 2 disclose a rocket exhaust probe 10 for collecting an unbiased sample of particles and gas from a supersonic exhaust plume of a rocket. The probe is designed to withstand the extremely hostile environment of the rocket exhaust for a sample time of at least one second.

A shield plate 12 protects the exhaust probe 10 from the rocket blast except when it is actually collecting a sample. After rocket ignition, the shield 12 and the probe 10 are rotated together into the rocket plume flow from a storage position. This prevents probe damage which might occur from subjecting the probe to the debris and smoke common to rocket ignition. After the shield and probe are rotated into the rocket exhaust plume the shield is then momentarily rotated out of the plume flow to expose the probe in order that an exhaust sample may be taken. After the sample is taken the shield is replaced and the shield and probe are rotated out of the plume. The probe stand (not shown) can be made to be adjustable to accommodate a variety of rocket motors and rocket motor test stands. Rotating the shield 12 and probe can be done by any conventional pneumatic or electromechnical means.

Operation of the rocket exhaust probe 10 during sampling of the rocket plume can be more readily understood with reference to the cross section of FIG. 2. The rocket exhaust probe 10 comprises a nose tip 18, a nose holder 20, a central probe body 22 and a tail section 24. The probe 10 is affixed to a mounting tube 26 which is attached to a platform 28 that can be affixed to a probe stand.

The nose tip 18 is manufactured from tungsten which is able to withstand the rocket plume environment. The nose tip is manufactured with a sharp leading edge 30 surrounding its inlet 32 to prevent formation of a local bow shock. Typically a bow shock would form around a rounded nose wherein some of the airstream would be diverted to each side of inlet passage 32. In such a situation lighter particles would be diverted in a high proportion around the nose while heavier particles which would tend to flow straight through inlet 32 and bias the sample.

Inlet passage 32 of the nose tip 18 is contoured slightly to allow for boundary layer formation while avoiding choking of the flow stream in the probe entrance. Such choking would also result in the formation of a bow shockwave in front of the probe due to an inability of the internal passage to pass air quickly enough. This contouring consists of an opening out of the passage 32 to a large diameter at exit 34 to minimize the effect of the boundary layer on the central flow.

The sharp tungsten tip 18 is designed to efficiently capture or swallow a stream of 1 gram per second of plume in supersonic flow if the internal probe pressure is kept low. Similar tips may be designed to accept more or less flow depending upon the sizing of the rocket plume to be sampled.

The nose tip 18 is detachably held by the tip holder 20. The tip 18 has been made removable in view of the highly errosive rocket engine particulate flow it must withstand so that it can be removed for refurbishment or replacement. Tip holder 20 is rotatably mounted to the probe central body 22 so that it too can be easily removed for refurbishment.

The inlet stream that enters the probe through nose tip inlet 32 proceeds into a mixing chamber 36 inside the probe central body 22. The mixing chamber 36 is defined by the inner diametric surface of an instrumentation holder 37 which is securely fastened to an inner radius 39 of probe body 22.

The probe central body 22 is equipped with an inert gas entrance hole 38 which allows inert gas from the mounting tube 26 to enter into the probe body and mixing chamber 36. The mounting tube 26 is fed inert gas from a securely mounted inert gas line 40.

Inert gas which enters the probe body 22 through hole 38 flows around the instrumentation holder 37, past holder tip 42 and back into the mixing chamber 36 through passages 46. This portion of the inert gas forms as an ejector flow which reduces the tip exit 34 pressure at the mixing chamber 36 to below atmospheric, preferably to about 10 psia which encourages unrestricted flow through the nose tip.

The inert gas also flows forward and around the tip holder 20 to exit the probe at exit 44. This portion of the flow provides a cooling boundary layer which helps protect the material of the tip holder 20 from the environment of the rocket plume.

At the time it enters the mixing chamber 36 the exhaust gas flow is usually traveling in excess of four times the speed of sound, MACH 4 (i.e., MACH 4 is about 6000 feet per second for the heated exhaust gas). The cool inert gas is therefore injected into the air flow at about MACH 3 i.e., 3000 feet per second. Enough momentum is thereby maintained in the cold gas to prevent choking of the flow which would interfere with the ingestion of the rocket plume stream.

The mixing chamber 36 is sized to prevent the formation of a normal (perpendicular) supersonic shock as the gas stream slows down within the probe. The particular design conditions upon which design and operation of the probe is based are dictated by the environment of the rocket plume to be measured and the planned location of the probe within the plume. The mixing chamber is essentially a long constant diameter passage which encourages mixing between the hot sample and the cold inert gas. The chamber diameter and the gas flow rates have been chosen to avoid thermal choking of the combined gas stream.

Sufficient inert gas flow is provided to both cool and decelerate the inlet flow when it flows into the mixing chamber to mix with the inlet flow. Typically, the inert gas is used to cool the inlet stream to about 270° F. to preclude burning the particle collection filter 52. Mixing between the hot exhaust gas and cold inert gas also helps reduce the MACH number of the inlet flow to near sonic values due to the transfer of heat energy from hot to cold gas. In most applications a series of oblique shockwaves will also perform a portion of the gas stream deceleration in the mixing chamber. These oblique shock waves are far less disruptive to the flow and the exhaust particles carried therein than the high energy normal shocks that would occur with uncontrolled flow deceleration. The particle and gas mixture is also decelerated by friction forces as it contacts the internal surfaces of the mixing chamber 36. The particle velocities resulting from these forces are relatively low and the possibility of particle breakup upon impact with the particle filter is avoided.

The device shown in FIGS. 1 and 2 is intended to perform exploratory tests over a wide range of inlet MACH numbers and mass flows. This design, however, can be optimized to minimize internal shocks and produce a completely shockless, isentropic deceleration of the gas stream for a particular small range of inlet gas flows and MACH numbers.

Several inert gases or nearly inert gases can be used to cool and decelerate the inlet flow. Examples of such gases include helium, argon and nitrogen. Using inert gas prevents reaction of the exhaust particles with water vapor which might otherwise alter the particulate surfaces, change their methodology or hide the effects of conglomeration of particles. It is particularly important that collected particle structure be unchanged in order that particle interaction in the rocket exhaust and between rocket exhaust and internal rocket surfaces can be examined.

The decelerated mixed gas stream next leaves the mixing chamber 36 and enters diffusion chamber 50 in the tail section 24 of the probe. The large angle diffuser adapts the relatively small diameter flow stream for use with a relatively large flat commercial filter 52. Upon entering diffusion chamber 50 the airstream is generally slightly supersonic, however, a weak normal shock will generally occur decelerating the flow to subsonic values just past the diffusion chamber entrance. This weak shock has far less energy than would be found in an uncontrolled deceleration of the airstream and should not generally disrupt or bias the particles carried by the stream. This weak normal shock raises the static gas pressure in the diffusion chamber to that which is sufficient to force the airstream through the particle filter 52. Since the normal shock in the diffuser raises the static pressure to about 30 psia there is sufficient impulse to push the airstream through the filter 52 which exits to atmospheric pressure (14.7 psia).

Filter 52 is preferably a removable submicron filter capable of collecting up to a gram of particulate without creating undue filter back pressure loss. Filters of this type are made comxercially of acetate nitro cellulose by Millipore Corporation of Bedford, Mass. Various commercial filters can be chosen based on the mass flow rate and the sizing of particles to be collected. In the most stringent instance the preferred filter is a 0.025 micron filter which collects all particles larger than 0.025 microns (uM).

After the particle sample has been taken the submicron filter 52 is removed from the probe by releasing nuts 54 and the rocket plume particulates are analyzed according to size and composition. A rocket plume gas sample may be compared to the matter found in the particulate. This gas sample can be taken upstream or downstream the filter 52 by a fluid connection and a collection tank. A typical fluid connection 55 (upstream of the filter) is shown in FIG. 1.

In order to monitor the inert gas flow during exhaust flow ingestion so that it can be determined if proper mixing deceleration and cooling have occurred, three pressures are measured within the probe. These pressures are measured using commercial pressure transducers. The first pressure measurement is taken at point 56, near the discharge point 34 of the nose tip, and is used to measure the discharge pressure of the exhaust gas inlet stream. The second pressure measurement is taken at point 58 and is used to measure the supply pressure of the inert gas in order to determine the precise cooling gas mass flow rate into the mixing chamber. The third pressure measurexent is taken at point 60 and is used is used to determine the pressure at the inlet of the filter 56 in order to monitor particle collection conditions. These static pressure sensors can also be used in conjunction with thermocouples which monitor flow temperature throughout the probe. Since these measuring devices can be routed through the instrumentation holder 37 they can be protected from the hostile environment of the plume and require no special shielding.

This invention solves the problems associated with collecting an unbiased particle and gas sample from rocket nozzle flow fields. In the past, sample bias has occured due to the great distance required between the probes and the rocket nozzle, usually in excess of 50 feet. This invention is made for use in the plume itself i.e., within a few feet of the rocket nozzle. Other sample collection problems which have occurred as a result of the inability to use a conventional submicron filter. This has been solved by the cooling and decelerating means used in the probe which make the flow acceptable to a conventional filter. Further, chemical bias which occurred through a mixture of rocket exhaust with standard atmosphere is avoided since the rocket stream is quenched with inert gas. This prevents changes in the characteristics of the rocket stream prior to collection of particulate and gas samples. Finally this probe avoids strong normal supersonic shocks from disrupting the particulate matter.

In a typical series of rocket tests particles are initially collected by the probe in the least severe environment of the rocket plume. Subsequent tests are performed in more severe areas of the plume including the area immediately adjacent the nozzle. In between tests both the tungsten nose tip and the preferrably steel tip holder can be easily remachined and refurbished if that is required.

Particulate mass flux can be determined by comparing the amount of particles collected by the filter to the nose tip capture area and exposure time. This, of course, is an important way of determining rocket efficiency and uniformity of combustion. Collection of data of this nature and studies of particulates emitted by the rocket plume help in the design of improved high efficiency rockets as well as increase reliability of existing rockets. All these factors can help insure success of the nation's defense and space endeavors.

While the invention has been particularly described with reference to the preferred embodiments thereof, it will be understood by those skilled in the art that various changes in substance and form can be made therein without having departed from the spirit and the scope of the invention as detailed in the appended claims.

I claim:
1. An exhaust probe comprising:
   (a) a sharpened inlet tip for ingesting heated exhaust gas;
   (b) an inert coolant gas for cooling said probe;
   (c) a mixing chamber connected to said inlet tip for mixing and decelerating said exhaust gas and said inert coolant gas;
   (d) an expansion chamber connected to said mixing chamber for further decelerating and cooling said exhaust gas; and
   (e) a filter screen attached to said expansion chamber for collecting particle samples from said exhaust gas.

2. The exhaust probe of claim 1 wherein said coolant gas is used to reduce air pressure inside the probe in order to draw exhaust gas into said probe.

3. The exhaust probe of claim 1 wherein said coolant gas mixes with said exhaust gas in said mixing chamber in a manner which reduces exhaust gas speed gradually and thereby minimizes disturbances of particulate material.

4. The exhaust probe of claim 1 further comprising a pressure sensor for sensing inlet gas pressure.

5. The exhaust probe of claim 1 wherein a portion of said exhaust gas is diverted to a fluid connection for collection.

6. A rocket plume exhaust probe comprising:
   (a) a sharpened inlet tip constructed of a material capable of withstanding elevated temperatures and for ingesting a portion of a rocket plume exhaust;
   (b) a probe body receiving said inlet tip;
   (c) a mixing chamber positioned within said probe body for mixing said rocket plume exhaust with a coolant gas in order to cool and decelerate said rocket plume exhaust;
   (d) an expansion chamber positioned aft of said mixing tube for further decelerating said rocket plume exhaust; and (e) a filter screen for collecting solid particles from said rocket plume exhaust.

7. The rocket plume exhaust probe of claim 6 wherein said inlet tip is constructed of tungsten.

8. The rocket exhaust probe of claim 6 wherein said coolant gas is used to reduce static gas pressure in said mixing chamber in order to draw exhaust gas into said probe.

9. The rocket exhaust probe of claim 6 further comprising a pressure sensor for sensing inlet gas pressure.

10. The rocket exhaust probe of claim 6 wherein a portion of said coolant gas is routed through said inlet and exhausted in a manner which cools the exterior of the probe body.

11. The rocket exhaust probe of claim 6 wherein said filter screen is a submicron mesh filter.

12. The rocket exhaust probe of claim 11 wherein said filter screen is an acetate nitro cellulose filter.

13. The rocket exhaust probe of claim 6 further comprising a pressure sensing tap adjacent to said filter screen for monitoring gas pressure at said filter screen.

14. A method of collecting rocket exhaust stream data comprising the steps of:

(a) igniting a rocket engine to create a rocket exhaust plume;

(b) rotating an exhaust probe and an exhaust probe shield into said rocket exhaust plume;

(c) rotating said exhaust probe shield away from said exhaust probe in order to expose said exhaust probe to said rocket exhaust plume so that a portion of said rocket exhaust is ingested by said exhaust probe and data is collected;

(d) rotating said exhaust probe shield into a position which shields said rocket exhaust probe from said rocket exhaust plume; and (e) rotating said exhaust probe and said exhaust probe shield out of said rocket exhaust plume.

15. The method of claim 14 wherein said rocket exhaust probe collects particulate matter.

16. The method of claim 14 wherein an inert gas is mixed with said portion of said rocket exhaust ingested by said probe in order to cool and decelerate said portion of said rocket exhaust.

17. The method of claim 14 wherein an inert exhaust gas is injected into and exhausted from said exhaust probe in a manner which lowers the static gas pressure therein.

* * * * *